United States Patent [19]

Schunck et al.

[11] Patent Number: 5,521,510
[45] Date of Patent: May 28, 1996

[54] PROCESS FOR MONITORING FOR ORGANIC IMPURITIES IN WATER

[75] Inventors: Günter Schunck, Maintal; Joachim Wasel-Nielen; Christian Lauer, both of Frankfurt; Werner Melzer, Liederbach, all of Germany

[73] Assignee: Hoechst Aktiengesellschaft, Frankfurt, Germany

[21] Appl. No.: 319,418

[22] Filed: Oct. 6, 1994

[30] Foreign Application Priority Data

Oct. 8, 1993 [DE] Germany ................. 43 34 434.8

[51] Int. Cl.⁶ ..................... G01N 27/04; G01N 33/18
[52] U.S. Cl. ................. 324/439; 324/722; 73/61.41; 436/150; 205/787
[58] Field of Search ..................... 324/439, 450, 324/722; 73/61.41, 61.42, 61.43; 204/400, 153.1; 436/150

[56] References Cited

U.S. PATENT DOCUMENTS

| 3,955,403 | 5/1976 | Bodmer | 73/61.41 |
| 4,251,220 | 2/1981 | Larson et al. | 436/150 X |
| 4,801,551 | 1/1989 | Byers et al. | 436/150 X |
| 4,822,744 | 4/1989 | Bellows | 436/150 X |
| 5,218,856 | 6/1993 | Doyle | 73/61.41 X |
| 5,282,381 | 2/1994 | Krone-Schmidt | 73/61.41 |

FOREIGN PATENT DOCUMENTS

| 0124850 | 6/1986 | Japan | 73/61.41 |
| 0154953 | 6/1988 | Japan | 73/61.41 |

*Primary Examiner*—Kenneth A. Wieder
*Assistant Examiner*—Diep Do
*Attorney, Agent, or Firm*—Curtis, Morris & Safford

[57] ABSTRACT

In the process for monitoring water, in particular boiler feed water, for organic impurities by measuring the conductivity, a part stream is diverted from a sample water stream and its conductivity is measured. The other part stream evaporated at 300°–500° C.; the vapor is thermally treated at temperatures of 800°–1000° C.; the treated vapor is condensed and the conductivity of the condensate is measured. Subsequently the difference between the measured conductivities is taken.

9 Claims, 1 Drawing Sheet

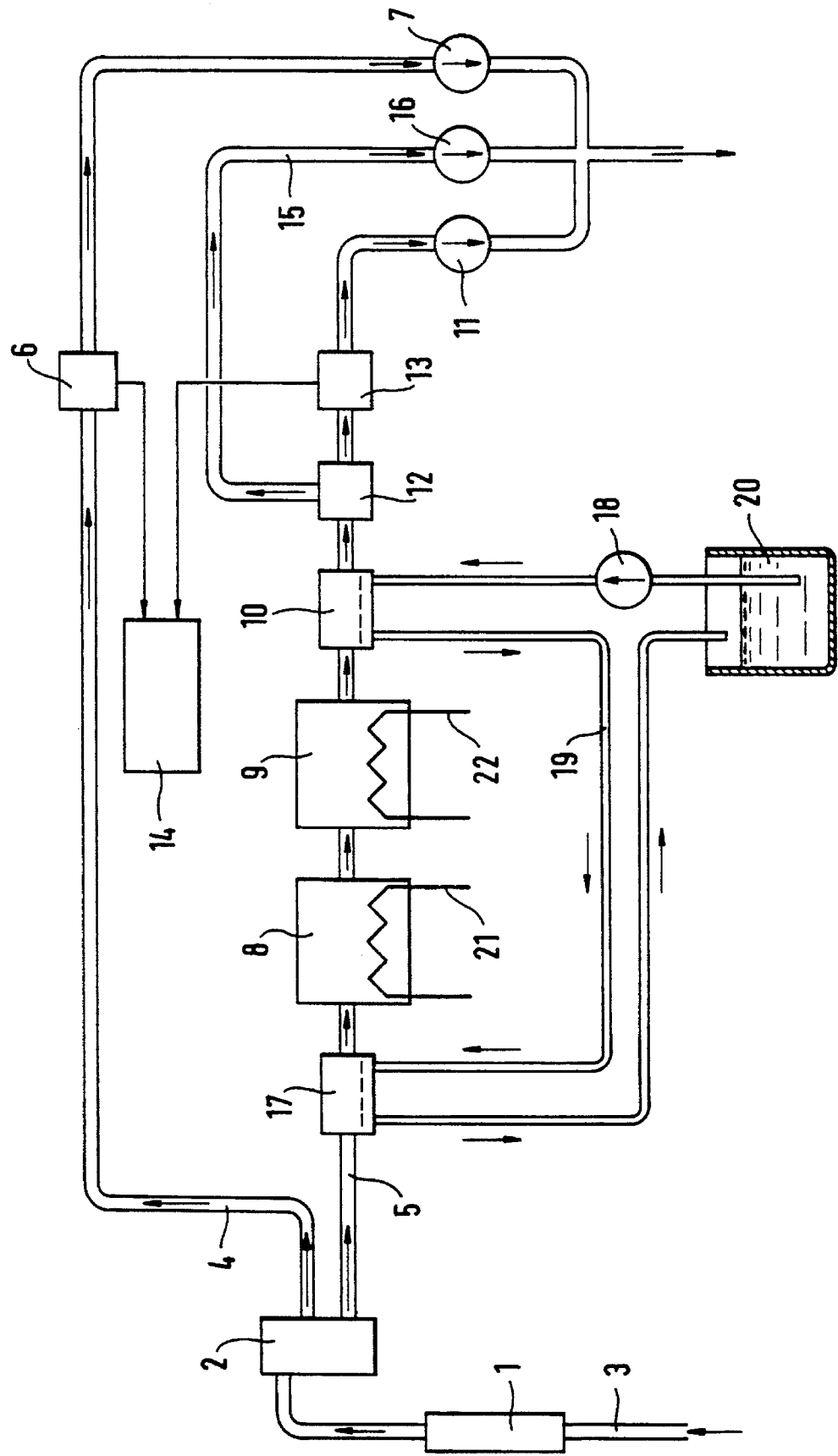

PROCESS FOR MONITORING FOR ORGANIC IMPURITIES IN WATER

FIELD OF THE INVENTION

The invention relates to a process for monitoring water, in particular boiler feed water, for organic impurities by measuring the conductivity.

The invention further relates to a device for carrying out the process.

BACKGROUND OF THE INVENTION

Impurities, in particular dissolved halogenated hydrocarbons, must be avoided in boiler feed water, as they cause corrosion in the steam boiler. The DOC (dissolved organic carbon) process is known for the detection of dissolved organic impurities. A disadvantage of this process is that volatile organics and heteroatoms, e.g. acid formers, such as chlorine and sulfur compounds, are not detected.

A process is further known in which the thermal conversion taking place in the boiler is to be imitated in a UV reactor. In this method the conductivity of the water is measured after irradiation. A disadvantage of this process is that, as a result of the UV oxidation, the conversion of e.g. halogenated hydrocarbons to soluble, dissociable components does not take place to the desired extent.

SUMMARY OF THE INVENTION

It is the wish of the invention to provide for a remedy here. The object is achieved by a process of the type mentioned at the outset, which comprises diverting a part stream from a sample water stream and measuring the conductivity, evaporating the other part stream at 300°–500° C., treating the steam thermally at temperatures of 800°–1000° C., condensing the treated steam, measuring the conductivity of the condensate and taking the difference between the measured conductivities.

BRIEF DESCRIPTION OF THE DRAWINGS

The FIGURE illustrates a schematical representation of one embodiment of the present invention.

DESCRIPTION OF THE INVENTION

The process can be further improved if after condensing the steam any gas present is separated off and condensate and gas are fed separately. The sample can also be passed through an ion exchanger before division.

For carrying out the process according to the invention, a device is suitable wherein two conductivity measuring cells are connected after a sample water stream divider, an evaporator, a reactor and a condenser being arranged between the sample water stream divider and one of the conductivity measuring cells in the measuring cell direction, and the measuring cells being connected to an electronic measurement processing arrangement.

A gas separator can be connected after the condenser, and a steam baffle can be connected before the evaporator and an ion exchanger before the sample divider. Feed arrangements for the sample water streams can be connected after the measuring cells.

The advantages of the process are essentially to be seen in that the thermal process is identical to the processes in the steam boiler and thus produces a direct statement about the extent of a damaging action.

In the following, the invention is illustrated in greater detail with the aid of a flow diagram (the Figure). A sample water stream (pipeline 3) is divided into two sample water part streams (pipelines 4 and 5) in a sample water stream divider (2) after passing through an ion exchanger (1). The first part stream (pipeline 4) is taken from the sample water stream divider (2) by means of a pump (7) and fed to an optionally thermostated conductivity measuring cell (6), where the electrical conductivity is measured. The second sample water part stream (pipeline 5) is taken from the sample water stream divider (2) by means of a pump (11) and fed to an evaporator (8), where it is evaporated at 300°–500° C. The steam is then treated thermally at temperatures of 800°–1000° C. and almost atmospheric pressure in a reactor (9), the organic constituents decomposing. The treated steam is condensed in an after-connected condenser (10), the decomposed constituents, essentially acids, dissociating and leading to a conductivity increase. The condensate is fed, optionally after separation of gas in a gas separator (12), to an optionally thermostatted conductivity measuring cell (13). The conductivities measured in the measuring cells (6) and (13) are processed in a measurement processing arrangement (14). The measurement signal of the conductivity cell after the reactor is either used as a measure of the contamination or—in the case of possibly varying baseline conductivity—the difference between the two conductivity values is used as a measure of the contamination, in particular from halogenated organic compounds. Gas which is possibly separated off is taken from the gas separator (12) via pipeline (15) by means of pump (16). It may be expedient to connect a steam baffle (17) before the evaporator (8). The pump (18), pipeline (19) and reservoir (20) are intended to indicate a coolant circulation, the reference figures (21) and (22) in each case refer to the energy supply arrangement for the evaporator (8) and reactor (9). The separate aspiration of gas and condensate from the gas separator (12) in combination with the preconnected steam baffle (17) causes a damping of the pressure shocks occurring as a result of the evaporation of the sample water, which can lead to severe variations in the flow and would thus adversely affect the flow-dependent conductivity measurement. Moreover, severe measurement variations (noise), which would likewise affect the signal, caused by small gas bubbles on the conductivity electrodes as a result of adhesion and detachment are avoided to the greatest possible extent.

We claim:

1. A process for monitoring organic impurities in water by measuring conductivity, which comprises diverting a first part stream from a sample water stream and measuring the conductivity of the first part stream, evaporating a second part stream at 300°–500° C. to produce steam, treating the steam thermally at temperatures of 800°–1000° C., condensing the treated steam to form condensate, measuring the conductivity of the condensate and taking the difference between the measured conductivities of the first part stream and the condensate.

2. The process as claimed in claim 1, wherein after condensing the treated steam any gas present is separated off and the condensate and the gas are fed separately.

3. The process as claimed in claim 1 or 2, wherein the sample water stream is passed through an ion exchanger before division.

4. A device for carrying out the process as claimed in claim 1, wherein two conductivity measuring cells (6, 13) are connected after a sample water stream divider (2), an evaporator (8), a reactor (9) and a condenser (10) being arranged in series connection between the sample water stream divider (2) and one of the conductivity measuring cells (6, 13) in the measuring cell direction, and the measuring cells (6, 13) being connected to an electronic measurement processing arrangement (14).

5. The device as claimed in claim 4, wherein a gas separator (12) is connected after the condenser (10).

6. The device as claimed in claim 4 or 5, wherein a steam baffle (17) is connected before the evaporator (8).

7. The device as claimed in claim 4, wherein an ion exchanger (1) is connected before the sample water stream divider (2).

8. The device as claimed in claim 4, wherein pumps (7, 11) for the sample water part streams are connected after the measuring cells (6, 13).

9. The process as claimed in claim 1, wherein the water is boiler feed water.

* * * * *